United States Patent
Shirahase et al.

(12)

(10) Patent No.: US 6,201,011 B1
(45) Date of Patent: Mar. 13, 2001

(54) THERAPEUTIC AGENT FOR ALLERGIC DERMATITIS

(75) Inventors: Hiroaki Shirahase, Nagaokakyo; Akihisa Yoshimi, Takatsuki; Shohei Nakamura, Kyoto; Mamoru Kanda, Nagaokakyo, all of (JP)

(73) Assignee: Kyoto Pharmaceutical Industries, Ltd., Kyoto (JP)

( * ) Notice: Subject to any disclaimer, the term of this patent is extended or adjusted under 35 U.S.C. 154(b) by 0 days.

(21) Appl. No.: 09/242,894

(22) PCT Filed: Aug. 25, 1997

(86) PCT No.: PCT/JP97/02952

§ 371 Date: Feb. 26, 1999

§ 102(e) Date: Feb. 26, 1999

(87) PCT Pub. No.: WO98/08504

PCT Pub. Date: Mar. 5, 1998

(30) Foreign Application Priority Data

Aug. 30, 1996 (JP) .................................... 8-230923

(51) Int. Cl.$^7$ ............................ A01N 43/16; A61K 31/35
(52) U.S. Cl. ............................................. 514/456; 514/886
(58) Field of Search ..................... 514/456, 886

(56) References Cited

U.S. PATENT DOCUMENTS 4,847,286 * 7/1989 Tamaki et al. ............... 514/456

FOREIGN PATENT DOCUMENTS

| 0 084 190 | 7/1983 | (EP) . |
| 1 593 097 | 7/1981 | (GB) . |
| 62-42981 | 2/1987 | (JP) . |

OTHER PUBLICATIONS

S. Nakamura et al., "Effects of N–556 on Experimental Allergy Models in Rats", Japanese Journal of Allergology, vol. 38, No. 12, pp. 1621–1628, 1990.

A. Yoshimi et al., "Absorption Mechanism of 1,3–Bis(2–ethoxycarbonychromon–5–yloxy)–2–((S)–lysyloxy)propane Dihydrochloride (N–556), a Prodrug for Oral Delivery of Disodium Cromoglycate", Biological & Pharmaceutial Bulletin, vol. 16, No. 4, pp. 375–378, 1993.

H. Kimata et al., "Effect of Topical Cromoglycate Solution on Atopic Dermatitis: Combined Treatment of Sodium Cromoglycate Solution with the Oral Anti–Allergic Medication, Oxatomide", European Journ of Pediatrics, vol. 153, No. 2, pp. 66–71, 1994.

L. Businco et al., "Evaluation of the Efficacy of Oral Cromolyn Sodium or an Oligoantigentic Diet in Children with Atopic Dermatitis: A Multicenter Study of 1085 Patients", Journal of Investigational Allergology & Clinical Immunology, vol. 6, No. 2, pp. 103–109, 1996.

DATABASE WPI, Section Ch, Week 199642, Derwent Publications Ltd., London, GB; Class B05, An 1996–421899 XP002143925 & JP 08 208487 A ( Sekisui Chem. Ind. Co., Ltd.) Aug. 13, 1996 *abstract*.

* cited by examiner

*Primary Examiner*—S. Mark Clardy
*Assistant Examiner*—Konata M. George
(74) *Attorney, Agent, or Firm*—Wenderoth, Lind & Ponack, L.L.P.

(57) ABSTRACT

A therapeutic agent for allergic dermatitis caused by type IV allergic reaction, which contains diethyl L-lysylcromoglycate of the formula:

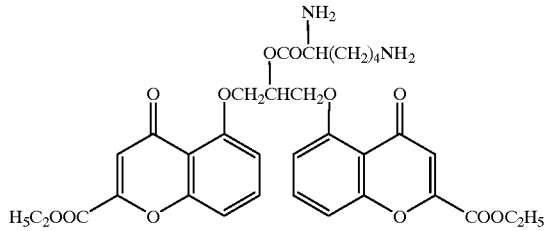

or a nontoxic salt thereof as an active ingredient. This therapeutic agent for allergic dermatitis is effective for the treatment of allergic dermatitis caused by type IV allergic reaction, such as contact dermatitis mainly induced by type IV allergic reaction and atopic dermatitis induced by type I and type IV allergic reactions.

25 Claims, No Drawings

THERAPEUTIC AGENT FOR ALLERGIC DERMATITIS

TECHNICAL FIELD

The present invention relates to a therapeutic agent for allergic dermatitis caused by type IV allergic reaction, which comprises diethyl L-lysylcromoglycate or a nontoxic salt thereof as an active ingredient. More particularly, the present invention relates to a therapeutic agent for contact dermatitis and to a therapeutic agent for atopic dermatitis.

BACKGROUND ART

Typical allergic dermatitis includes contact dermatitis, atopic dermatitis and the like.

The contact dermatitis is an inflammation of the skin, which is developed by the contact of a substance with the skin. The onset of the disease is seen when, for example, a certain substance, such as plant (e.g., lacquer and the like), cosmetics, detergent, clothes, commercially available external drug and the like, comes into contact with the skin and when the substance irritates beyond the resistance threshold value of the individual or when the individual has been sensitized with the substance in contact. The onset of the contact dermatitis is caused by physicochemical properties of the substance, sensitization activity, contact frequency, disposition of the individual and the like. The disease type includes irritant dermatitis, phototoxic dermatitis, allergic dermatitis, photoallergic dermatitis, contact urticaria, systemic contact-type dermatitis and the like. The clinical symptoms of contact dermatitis include acute eczema accompanied by erythema, edema, papula, vesicle, erosion, itching and the like, and repetition thereof develops eczema accompanying lichenification and infiltration. The mechanism of the onset of these diseases is considered to involve type IV allergic reaction (delayed type allergic reaction) caused by T cell. The type IV allergic reaction is induced by the reaction of sensitized T cell and antigen, which releases lymphokine from the sensitized T cell to cause cytotoxicity and the like, which in turn induces this allergic reaction.

The atopic dermatitis is developed by exogenous disposition, namely, by various antigens, since the subject has an atopic disposition which is hypersensitivity against a certain substance. The clinical symptoms include marked itching, skin hypertrophy, infiltration, lichenification and the like. The mechanism of the onset of this disease has been said to include type I allergic reaction (immediate hypersensitivity) involving IgE, but it is inconclusive. In recent years, type IV allergic reaction has been considered to be responsible for the onset of this disease, and in fact, the clinical symptoms of this disease are extremely similar to the symptoms of the above-mentioned contact dermatitis allegedly caused by type IV allergic reaction.

Currently, anti-histamine agents and steroidal agents have been used as therapeutic agent for contact dermatitis, and these and a part of the so-called antiallergic agents have been mainly used for atopic dermatitis.

Examples of anti-histamine agents include diphenhydramine hydrochloride, mequitazine, promethazine hydrochloride, chlorpheniramine maleate and the like, and they have been mainly used to reduce itchiness.

As the steroidal agents, prednisolone, hydrocortisone butyrate, dexamethasone valerate, betamethasone dipropionate, clobetasol propionate and the like have been used. While these show therapeutic effects, they also cause side effects of induced infection, secondary adrenal cortical insufficiency, diabetes, peptic ulcer, hirsutism, alopecia, pigmentation and the like, and they are remotely desirable therapeutic agents.

As the antiallergic agent, tranilast, ketotifen fumarate, oxatomide, azelastine hydrochloride and the like have been used. None of them shows satisfactory therapeutic effects and they are not used for contact dermatitis.

In general, conventional so-called antiallergic agents, such as tranilast, oxatomide, pemirolast potassium, repirinast, emedastine difumarate, epinastine hydrochloride and the like are either ineffective or fail to show satisfactory therapeutic effects on contact dermnatitis and atopic dermatitis that are considered to be mainly caused by type IV allergic reaction. This is postulated to be due to the inhibitory action of these so-called antiallergic agents only on type I allergic reaction (immediate hypersensitivity), in which IgE is involved, and failure to show type IV allergic reaction-inhibitory action (Kobayashi, K. et al.: Japan. J. Pharmacol. 63, 73–81 (1993), Takemori Omori et al.: Folia Pharmacol. Jpn. 80, 261–270 (1982), Yanagihara, Y. et al.: Japan. J. Pharmacol. 51, 93–100 (1989), Kazuo Takahashi et al.: Folia Pharmacol. Jpn. 88, 245–254 (1986), Tadayulk Saito et al.: Folia Pharmacol. Jpn. 89, 55–62 (1987), Kamei, C. et al.: Arzneim.-Forsch./Drug Res.41(II), 1150–1153).

Hence, a type IV allergic reaction-inhibitory action at the inflammation site is considered to be essential for the treatment of allergic dermatitis, particularly contact dermatitis and atopic dermatitis.

Incidentally, it has been documented that a compound of the formula (I):

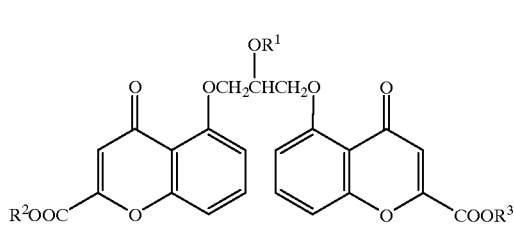

wherein $R^1$ is α-amino acid residue (ester bond) wherein amino may be substituted by lower alkyl and $R^2$ and $R^3$ are each lower alkyloxy or substituted or unsubstituted lower alkyl (hereinafter also referred to as cromoglycic acid derivative (I)), can be used as an antiallergic agent.

In the above-mentioned various situations, the development of a highly safe and highly effective therapeutic agent for allergic dermatitis caused by type IV allergic reaction, particularly a therapeutic agent for contact dermatitis and a therapeutic agent for atopic dermatitis, has been demanded.

It is therefore an object of the present invention to provide a therapeutic agent effective for allergic dermatitis, such as contact dermatitis caused by type IV allergic reaction and atopic dermatitis caused by type IV and type I allergic reactions, which is highly safe and can be administered orally.

DISCLOSURE OF THE INVENTION

The present inventors have conducted various studies in an attempt to achieve the above-mentioned objects and found that a cromoglycic acid derivative of the formula (II):

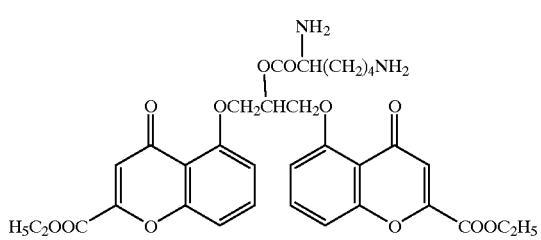

namely, diethyl L-lysylcromoglycate, and a nontoxic salt thereof are finely absorbed from the digestive tract and are effective for the treatment of allergic dermatitis such as contact dermatitis caused by type IV allergic reaction, atopic dermatitis caused by type I and type IV allergic reactions, and the like, which resulted in the completion of the present invention.

Accordingly, the present invention provides the following.

(1) A therapeutic agent for allergic dermatitis caused by type IV allergic reaction, which contains diethyl L-lysylcromoglycate or a nontoxic salt thereof as an active ingredient.

(2) A therapeutic agent for allergic dermatitis caused by type I and type IV allergic reactions, which contains diethyl L-lysylcromoglycate or a nontoxic salt thereof as an active ingredient.

(3) A therapeutic agent for contact dermatitis, which contains diethyl L-lysylcromoglycate or a nontoxic salt thereof as an active ingredient.

(4) A therapeutic agent for atopic dermatitis, which contains diethyl L-lysylcromoglycate or a nontoxic salt thereof as an active ingredient.

(5) The therapeutic agent of any of the above (1) to (4), which is in the form of an oral preparation.

(6) The therapeutic agent of any of the above (1) to (5), further containing an organic acid.

(7) The therapeutic agent of the above (6), wherein the organic acid is at least one organic carboxylic acid selected from the group consisting of maleic acid, fumaric acid, tartaric acid, citric acid, succinic acid, malic acid, oxalic acid, mandelic acid, malonic acid and benzoic acid.

(8) A pharmaceutical composition for treating allergic dermatitis caused by type IV allergic reaction, which contains diethyl L-lysylcromoglycate or a nontoxic salt thereof, and a pharmaceutically acceptable carrier.

(9) A pharmaceutical composition for treating allergic dermatitis caused by type I and type IV allergic reactions, which contains diethyl L-lysylcromoglycate or a nontoxic salt thereof, and a pharmaceutically acceptable carrier.

(10) A pharmaceutical composition for treating contact dermatitis, which contains diethyl L-lysylcromoglycate or a nontoxic salt thereof, and a pharmaceutically acceptable carrier.

(11) A pharmaceutical composition for treating atopic dermatitis, which contains diethyl L-lysylcromoglycate or a nontoxic salt thereof, and a pharmaceutically acceptable carrier.

(12) The pharmaceutical composition for treatment of any of the above (8) to (11), which is in the form of an oral preparation.

(13) The pharmaceutical composition for treatment of any of the above (8) to (12), further containing an organic acid.

(14) The pharmaceutical composition for treatment of the above (13), wherein the organic acid is at least one organic carboxylic acid selected from the group consisting of maleic acid, fumaric acid, tartaric acid, citric acid, succinic acid, malic acid, oxalic acid, mandelic acid, malonic acid and benzoic acid.

(15) A method for treating allergic dermatitis caused by type IV allergic reaction, comprising administering an effective amount of diethyl L-lysylcromoglycate or a nontoxic salt thereof to a patient.

(16) Use of diethyl L-lysylcromoglycate or a nontoxic salt thereof for treating allergic dermatitis caused by type IV allergic reaction.

(17) Use of diethyl L-lysylcromoglycate or a nontoxic salt thereof for the production of a therapeutic medicament for allergic dermatitis caused by type IV allergic reaction.

(18) A commercial package comprising the therapeutic pharmaceutical composition of any of the above (8) to (14) and a written matter, said written matter stating that the pharmaceutical composition can be or should be used for the treatment of allergic dermatitis caused by type IV allergic reaction.

In the present invention, conversion of diethyl L-lysylcromoglycate into a nontoxic salt to be mentioned later, particularly acid addition salt, results in increased absorption efficiency and facilitated stabilization, isolation and formulation of oral preparation of diethyl L-lysylcromoglycate.

In the present invention, moreover, oral administration of diethyl L-lysylcromoglycate in the presence of an organic acid leads to a strikingly increased solubility of diethyl L-lysylcromoglycate in the digestive tract. Therefore, the therapeutic agent for allergic dermatitis of the present invention preferably contains an organic acid as exemplified later.

Diethyl L-lysylcromoglycate is a known compound and can be produced by a method known in the art. For example, it can be produced by reacting diethyl cromoglycate and L-lysine.

L-lysine is subjected to the present reaction as it is as a free carboxylic acid or a reactive derivative thereof.

Diethyl L-lysylcromoglycate preferably forms a nontoxic salt (acid addition salt) at its amino acid residue. The acid to be used for forming such nontoxic salt is not particularly limited as long as it can form a salt with an amino acid residue and it is a pharmaceutically acceptable acid. Examples of such acid include mineral acids such as hydrochloric acid, sulfuric acid, phosphoric acid, nitric acid and the like and organic acid such as oxalic acid, fumaric acid, maleic acid, citric acid, tartaric acid, methanesulfonic acid, toluenesulfonic acid and the like. By converting to such salt, the absorption from the digestive tract can be further improved and production of the preparation can be facilitated.

The diethyl L-lysylcromoglycate or a nontoxic salt thereof produced as above is diluted with a pharmaceutical excipient according to a known method to give a therapeutic agent for allergic dermatitis, such as a therapeutic agent for contact dermatitis, a therapeutic agent for atopic dermatitis and the like, particularly, an oral therapeutic agent for allergic dermatitis. Dilution is performed according to a method known in the art such as mixing. Examples of excipient include starch, lactose, sugar, calcium carbonate, calcium phosphate and the like.

It is preferable to further add an organic acid to the therapeutic agent for allergic dermatitis for an enhanced solubility of the therapeutic agent for allergic dermatitis in the digestive tract, absorption into blood and delivery into the skin. This organic acid is subject to no particular limitation as long as it is pharmaceutically acceptable, and is preferably exemplified by organic carboxylic acids such as maleic acid, fumaric acid, tartaric acid, citric acid, succinic acid, malic acid, oxalic acid, mandelic acid, malonic acid, benzoic acid and the like. The content of the organic acid is generally 0.05–6 moles, preferably 0.05–3 moles, per mole of diethyl L-lysylcromoglycate.

The therapeutic agent for allergic dermatitis may contain other additives where necessary. Examples of preferable additive include binders (e.g., starch, acacia, carboxymethylcellulose, hydroxypropylcellulose, crystalline cellulose and the like), lubricants (e.g., magnesium stearate, talc and the like), disintegrators (e.g., calcium carboxymethylcellulose, talc and the like), and the like. Various ingredients are added and the mixture can be prepared into a dosage form suitable for oral administration, such as capsule, tablet, fine granule, granule, dry syrup and the like according to a known method. It is particularly preferable to prepare tablets.

The therapeutic agent for allergic dermatitis obtained by the present invention has anti-type I allergic activity and anti-type IV allergic activity and shows high absorption from the digestive tract and high delivery to the skin. Thus, the agent can be used as oral therapeutic agent for allergic dermatitis.

When this therapeutic agent is orally administered, the daily dose is desirably divided into 1–3 doses and applied by oral administration. While the dose varies depending on the symptom, age, body weight and the like of patients, 20–600 mg daily of diethyl L-lysylcromoglycate or a nontoxic salt thereof, which is the active ingredient, can be administered in a single dose to 3 doses.

EXAMPLES

The present invention is explained in more detail in the following by way of Examples, to which the present invention is not limited.

Example 1

Synthesis of Diethyl L-lysylcromoglycate Dihydrochloride (1) Diethyl cromoglycate (524 mg), di-t-butoxycarbonyl-L-lysine (520 mg) and dimethylaminopyridine (61 mg) are added to methylene chloride (10 ml). N,N-Dicyclohexylcarbodiimide (310 mg) is added at 0° C. and the mixture is stirred at the same temperature for 30 minutes and at room temperature for 6 hours. The precipitated urea compound is filtrated and the filtrate is concentrated. The concentrate is purified by silica gel column chromatography to give di-t-butoxycarbonyl diethyl L-lysylcromoglycate (580 mg, yield 68%).

IR (KBr, cm$^{-1}$) 1740, 1710, 1690, 1655
NMR (CDCl$_3$, δ ppm)

1.41 (18H, s, —C(CH$_3$)$_3$)
1.41 (6H, t, J=7Hz, —CH$_2$C$\underline{H}_3$)
1.4–2.1 (6H, m, —(CH$_2$)$_3$—)
2.8–3.3 (2H, m, —C$\underline{H}_2$NH—)

3.9–4.4(1H, m, —C$\underline{H}$NH—)

4.43 (4H, q, J=7Hz, —CH$_2$C$\underline{H}_3$)

4.3–4.8(4H, m, —CH$_2$CHC$\underline{H}_2$—)

4.7–5.5 (2H, m, —NH—)

5.4–5.9(1H, m, —CH$_2$C$\underline{H}$CH$_2$)

6.87 (2H, s, cromone 3-position —H)
6.8–7.4 (4H, m, cromone 6-position, 8-position —H)
7.58 (2H, t, J=9Hz, cromone 7-position —H)

(2) The compound (470 mg) obtained in (1) is dissolved in formic acid (1.1 ml). 1.4 M Hydrogen chloride-dioxane solution (2.8 ml) is added under ice-cooling and the mixture is stirred at room temperature for 30 minutes. The reaction mixture is poured into isopropyl ether and the precipitated product is collected by filtration to give diethyl L-lysylcromoglycate dihydrochloride (351 mg, yield 88%).

IR (KBr, cm$^{-1}$) 1740
NMR (DMSO-d$_6$, δ ppm)

1.34 (6H, t, J=7Hz, —CH$_2$C$\underline{H}_3$)
1.4–2.2 (6H, m, —(CH$_2$)$_3$—)
2.3–3.0 (2H, m, —C$\underline{H}_2$NH$_3^+$)

3.7–4.2(1H, m, —C$\underline{H}$NH$_3^+$)

4.36 (4H, q, J=7Hz, —CH$_2$CH$_3$)

4.3–4.9(4H, m, —CH$_2$CHC$\underline{H}_2$—)

5.4–5.9(1H, m, —CH$_2$C$\underline{H}$CH$_2$—)

6.72, 6.74 (2H, s, cromone 3-position —H)
7.12, 7.19 (4H, d, J=9Hz, cromone 6-position, 8-position —H)
7.74 (2H, t, J=9Hz, cromone 7-position —H)
7.5–9.0 (6H, br, —NH$_3^+$)

Experimental Example 1

Type IV Allergic Dermatitis-inhibitory Action by Diethyl L-lysylcromoglycate Dihydrochloride Male 6-week-old IRC mice (Charles River) were divided into two groups of control and administration group containing 10 mice each. Distilled water (10 ml/kg) was administered to the control group and diethyl L-lysylcromoglycate dihydrochloride (100 mg/kg) was administered to the administration group twice a day for 14 days. After the first administration at day 8 of the administration, pentobarbital sodium (55 mg/kg) was intraperitoneally administered to each mouse and the abdomen was shaved. 5% Picryl chloride (50 μl) dissolved in acetone-olive oil (mixing ratio, 1:4) was applied to the shaved portion (diameter about 2 cm). After the first administration at day 5 after application (day 12 of administration), all mice were ether anesthetized and the thickness of both auricles was measured with a dial thickness gauge (Mitutoyo Co.). 5% Picryl chloride (10 μl) dissolved in acetone-olive oil (mixing ratio, 1:4) was applied to the both sides of the right auricle and acetone-olive oil (10 µl, mixing ratio, 1:4) was applied to the both sides of the left auricle. After 48 hours from this antigen challenge, the thickness of both auricles was measured with a dial thickness gauge under ether anesthesia.

The difference between the thickness of the auricle coated with the solvent and the thickness of the auricle coated with the antigen was measured for each animal. The results are shown in the following Table 1. Comparison with the control group by t-test revealed significant inhibitory action on swelling of the auricle.

TABLE 1

Increase in thickness of auricle at 48 hours after coating of 5% picryl chloride (unit: mm)

|  | Control | Administration group (100 mg/kg) |
| --- | --- | --- |
| Difference in thickness of auricle after coating of antigen | 0.040 ± 0.006 | 0.015 ± 0.005** |

Each value is mean ± standard error (n = 8–10)
**: $p < 0.01$ (t-test relative to control group)

Male 6-week-old IRC mice (Charles River) were divided into two groups of control and administration group containing 10 mice each. Distilled water (10 ml/kg) was administered to the control group and diethyl L-lysylcromoglycate dihydrochloride (100 mg/kg) was administered to the administration group twice a day for 36 days. Before the second administration at day 8 of the administration, sodium pentobarbital (55 mg/kg) was intraperitoneally administered to each mouse and the thickness of both auricles was measured with a dial thickness gauge (Mitutoyo Co.). 0.2% Dinitrofluorobenzene (DNFB) dissolved in acetone-olive oil (mixing ratio 3:1) was applied by 25 µl to the both sides of the left and right auricles. After 24 hours from the application, the thickness of both auricles was measured under ether anesthesia with a dial thickness gauge. Thereafter, similar manipulation was repeated 4 times at a week interval.

Changes in the thickness of auricle of each mouse were calculated from the measurement values of the thickness of the both auricles before the first application. The average of changes in the thickness of the left and right auricles of each mouse was taken as the variation value of the animal. The results are shown in the following Table 2.

TABLE 2

Increase in thickness of auricle at 24 hours after repeated application of 0.2% DNFB (unit: mm)

|  | Control | Administration group (100 mg/kg) |
| --- | --- | --- |
| 24 hr after 1st application | 0.012 ± 0.001 | 0.013 ± 0.002 |
| 24 hr after 2nd application | 0.035 ± 0.003 | 0.020 ± 0.005* |
| 24 hr after 3rd application | 0.067 ± 0.007 | 0.038 ± 0.007** |
| 24 hr after 4th application | 0.082 ± 0.008 | 0.061 ± 0.010 |
| 24 hr after 5th application | 0.111 ± 0.010 | 0.061 ± 0.011** |

Each value is mean ± standard error (n = 8–9)
*: $p < 0.05$, **: $p < 0.01$ (t-test relative to control group)

The thickness of auricle before the first application was not different between the both groups. The repeated application of 0.2% DNFB resulted in increase in the thickness of auricle with time. Comparison with the control group by the t-test revealed significant inhibitory action on the swelling of the auricle after the second application in the administration group.

These results have clarified that the compound has an anti-type IV allergic activity and can make an effective therapeutic agent for allergic dermatitis such as contact dermatitis, atopic dermatitis and the like.

The Formulation Examples are given in the following.

Formulation Example 1

Tablets having the following composition are produced by a conventional method.

| Compound of Example 1 | 5 mg |
| --- | --- |
| Polyvinylpyrrolidone | 20 mg |
| Starch | 75 mg |
| Magnesium stearate | 2 mg |

Formulation Example 2

Tablets having the following composition are produced by a conventional method.

| Compound of Example 1 | 10 mg |
| --- | --- |
| Tartaric acid | 50 mg |
| Starch | 50 mg |
| Magnesium stearate | 3 mg |

Formulation Example 3

Tablets having the following composition are produced by a conventional method.

| Compound of Example 1 | 25 mg |
| --- | --- |
| Polyvinylpyrrolidone | 20 mg |
| Starch | 75 mg |
| Magnesium stearate | 2 mg |

Formulation Example 4

Tablets having the following composition are produced by a conventional method.

| Compound of Example 1 | 50 mg |
| --- | --- |
| Polyvinylpyrrolidone | 20 mg |
| Starch | 75 mg |
| Magnesium stearate | 2 mg |

Formulation Example 5

Tablets having the following composition are produced by a conventional method.

| Compound of Example 1 | 100 mg |
| --- | --- |
| Polyvinylpyrrolidone | 20 mg |
| Starch | 75 mg |
| Magnesium stearate | 2 mg |

INDUSTRIAL APPLICABILITY

Diethyl L-lysylcromoglycate and a nontoxic salt thereof to be used in the present invention show fine tissue migration to the skin and, when orally administered, are quickly absorbed from the digestive tract, delivered at high blood concentration and exert efficacy. These compounds have an anti-type IV allergic activity, and are effective for contact dermatitis mainly induced by type IV allergic reaction and atopic dermatitis induced by type I and type IV allergic reactions, on which conventional antiallergic agents have failed to produce sufficient effects. Therefore, these compounds can be used as an oral therapeutic agent effective for allergic dermatitis in general, in which type IV allergic reaction is involved, particularly allergic dermatitis such as dermatitis caused by the contact of antigenic substance with the skin, and the like.

This application is based on application No. 230923/1996 filed in Japan, the content of which is incorporated hereinto by reference.

What is claimed is:

1. A method for treating allergic dermatitis caused by type IV allergic reaction, comprising administering an effective amount of diethyl L-lysylcromoglycate or a nontoxic salt thereof to a patient in need thereof.

2. The method of claim 1, wherein L-lysylcromoglycate or the nontoxic salt thereof is administered orally.

3. A method for treating allergic dermatitis caused by type I and type IV allergic reactions, comprising administering an effective amount of diethyl L-lysylcromoglycate or a nontoxic salt thereof to a patient in need thereof.

4. The method of claim 3, wherein L-lysylcromoglycate or the nontoxic salt thereof is administered orally.

5. A method for treating contact dermatitis, comprising administering an effective amount of diethyl L-lysylcromoglycate or a nontoxic salt thereof to a patient in need thereof.

6. The method of claim 5, wherein L-lysylcromoglycate or the nontoxic salt thereof is administered orally.

7. A method for treating atopic dermatitis cause by type IV allergic reaction, comprising administering an effective amount of diethyl L-lysylcromoglycate or a nontoxic salt thereof to a patient in need thereof.

8. The method of claim 7, wherein L-lysylcromoglycate or the nontoxic salt thereof is administered orally.

9. A method for treating allergic dermatitis caused by type IV allergic reaction, comprising administering an effective amount of a pharmaceutical composition comprising diethyl L-lysylcromoglycate or a nontoxic salt thereof and a pharmaceutically acceptable carrier to a patient in need thereof.

10. The method of claim 9, wherein the pharmaceutical composition is administered orally.

11. The method of claim 10, wherein the pharmaceutical composition further comprises an organic acid.

12. The method of claim 11, wherein the organic acid is at least one organic carboxylic acid selected from the group consisting of maleic acid, fumaric acid, tartaric acid, citric acid, succinic acid, malic acid, oxalic acid, mandelic acid, malonic acid and benzoic acid.

13. A method for treating allergic dermatitis caused by type I and type IV allergic reactions, comprising administering an effective amount of a pharmaceutical composition comprising diethyl L-lysylcromoglycate or a nontoxic salt thereof and a pharmaceutically acceptable carrier to a patient in need thereof.

14. The method of claim 13, wherein the pharmaceutical composition is administered orally.

15. The method of claim 14, wherein the pharmaceutical composition further comprises an organic acid.

16. The method of claim 15, wherein the organic acid is at least one organic carboxylic acid selected from the group consisting of maleic acid, fumaric acid, tartaric acid, citric acid, succinic acid, malic acid, oxalic acid, mandelic acid, malonic acid and benzoic acid.

17. A method for treating contact dermatitis, comprising administering an effective amount of a pharmaceutical composition comprising diethyl L-lysylcromoglycate or a nontoxic salt thereof and a pharmaceutically acceptable carrier to a patient in need thereof.

18. The method of claim 17, wherein the pharmaceutical composition is administered orally.

19. The method of claim 18, wherein the pharmaceutical composition further comprises an organic acid.

20. The method of claim 19, wherein the organic acid is at least one organic carboxylic acid selected from the group consisting of maleic acid, fumaric acid, tartaric acid, citric acid, succinic acid, malic acid, oxalic acid, mandelic acid, malonic acid and benzoic acid.

21. A method for treating atopic dermatitis caused by type IV allergic reaction, comprising administering an effective amount of a pharmaceutical composition comprising diethyl L-lysylcromoglycate or a nontoxic salt thereof and a pharmaceutically acceptable carrier to a patient in need thereof.

22. The method of claim 21, wherein the pharmaceutical composition is administered orally.

23. The method of claim 22, wherein the pharmaceutical composition further comprises an organic acid.

24. The method of claim 23, wherein the organic acid is at least one organic carboxylic acid selected from the group consisting of maleic acid, fumaric acid, tartaric acid, citric acid, succinic acid, malic acid, oxalic acid, mandelic acid, malonic acid and benzoic acid.

25. A method for making a pharmaceutical composition for treatment of allergic dermatitis caused by type IV allergic reaction, which comprises preparing a composition comprising diethyl L-lysylcromoglycate or a nontoxic salt thereof with a pharmaceutically acceptable carrier.

* * * * *

UNITED STATES PATENT AND TRADEMARK OFFICE
CERTIFICATE OF CORRECTION

PATENT NO.   : 6,201,011 B1
DATED        : March 13, 2001
INVENTOR(S)  : Hiroaki Shirahase et al.

It is certified that error appears in the above-identified patent and that said Letters Patent is hereby corrected as shown below:

<u>Title page,</u>
Item [75] please insert -- Fumio Fukata, Osaka, Japan --

Signed and Sealed this

Fourteenth Day of May, 2002

Attest:

Attesting Officer

JAMES E. ROGAN
*Director of the United States Patent and Trademark Office*